1## United States Patent
Slautterback et al.

(10) Patent No.: US 6,994,681 B2
(45) Date of Patent: Feb. 7, 2006

(54) DISPOSABLE LINER FOR THE MULTI AFO/CONTRACTURE SPLINT

(75) Inventors: E. Gerald Slautterback, Miramar, FL (US); Donna F. Miller, Huntersville, NC (US)

(73) Assignee: FLA Orthopedics, Inc., Miramar, FL (US)

( * ) Notice: Subject to any disclaimer, the term of this patent is extended or adjusted under 35 U.S.C. 154(b) by 137 days.

(21) Appl. No.: 10/728,687

(22) Filed: Dec. 5, 2003

(65) Prior Publication Data

US 2005/0124924 A1   Jun. 9, 2005

(51) Int. Cl.
   *A61F 5/00*   (2006.01)
(52) U.S. Cl. ............................... 602/23; 27/62; 27/65
(58) Field of Classification Search .................. 602/14, 602/27, 28, 56, 62, 63, 65, 23; 604/367; 128/882, 892, 889
   See application file for complete search history.

(56) References Cited

U.S. PATENT DOCUMENTS

| 5,143,058 | A | * | 9/1992 | Luber et al. .................. 602/28 |
| 5,151,081 | A | | 9/1992 | Williams |
| 5,197,942 | A | | 3/1993 | Brady |
| 5,367,789 | A | * | 11/1994 | Lamont ........................ 36/9 R |
| 5,372,576 | A | | 12/1994 | Hicks |
| 5,453,082 | A | * | 9/1995 | Lamont ........................ 602/27 |
| 5,762,622 | A | * | 6/1998 | Lamont ........................ 602/65 |
| 5,853,380 | A | | 12/1998 | Miller |
| 5,885,236 | A | * | 3/1999 | Varn ............................ 602/27 |
| 5,961,477 | A | | 10/1999 | Turtzo |
| 6,056,712 | A | | 5/2000 | Grim |
| 6,060,059 | A | * | 5/2000 | St. Geme et al. ......... 424/190.1 |
| 6,067,987 | A | | 5/2000 | Scheinberg |
| 6,428,493 | B1 | * | 8/2002 | Pior et al. ..................... 602/10 |
| 6,432,073 | B2 | * | 8/2002 | Pior et al. ..................... 602/10 |
| 6,600,085 | B2 | * | 7/2003 | Sun et al. ..................... 602/56 |
| 2001/0031936 | A1 | | 10/2001 | Pior et al. |
| 2002/0138029 | A1 | | 9/2002 | Bacheldor |

\* cited by examiner

*Primary Examiner*—Henry Bennett
*Assistant Examiner*—Shumaya B. Ali
(74) *Attorney, Agent, or Firm*—Dougherty, Clements & Hofer

(57) ABSTRACT

The invention is a disposable liner for an AFO/contracture foot splint that is sufficiently soft and flexible so as to comfortably conform to body surfaces and provide a substantially close fit to prevent leakage. The liner has a fluid permeable layer, an absorbent layer, and a moisture-proof layer which is a liquid impervious back sheet disposed on the outer surface of the liner. The liner has a toe end, a foot region, a leg end, a leg region and a heel region. The foot region has winged extensions terminated with fastening elements for securing the foot region. The leg end of the liner has tabular extensions terminated with re-closable fastening elements for securing the leg region of the disposable liner to the leg. The heel region of the liner has an opening, which enables a portion of the wearer's heel to project through the heel region into heel "well" of a splint. The absorbent material in the absorbent layer may include an antimicrobial, as well as the nominal absorbents, such as cellulose and superabsorbents.

18 Claims, 2 Drawing Sheets

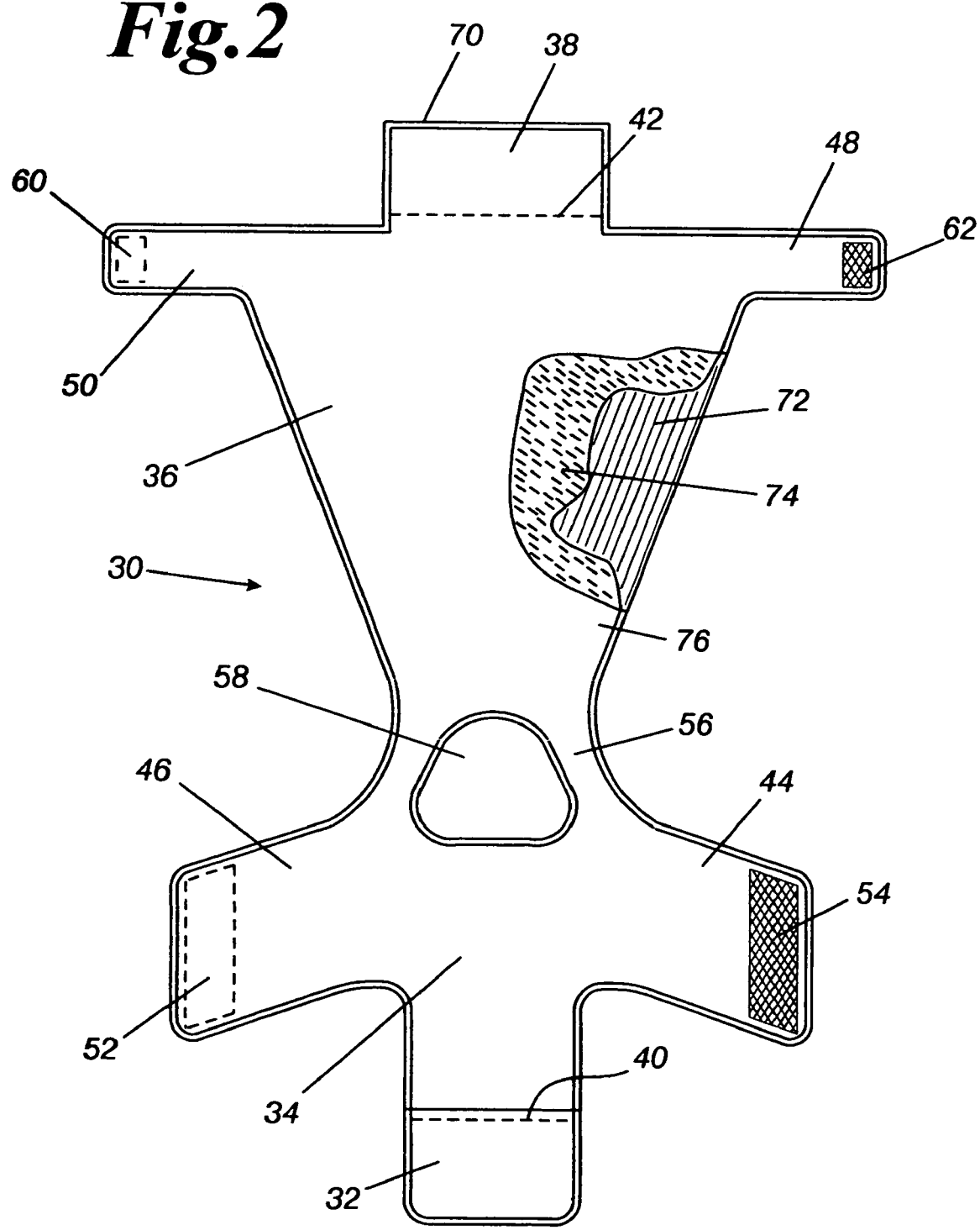

DISPOSABLE LINER FOR THE MULTI AFO/CONTRACTURE SPLINT

FIELD OF THE INVENTION

The present invention relates to Ankle Foot Orthosis (AFO) and splints having absorbent liners, and more particularly to AFO and splints having disposable absorbent liners.

BACKGROUND OF THE INVENTION

Many immobile and bed-ridden patients develop additional medical conditions while lying in bed that can result in serious health risks, prolonged recoveries and extended hospital stays. The two most common and preventable of these conditions are joint contractures and pressure sores. Preventing these conditions lead to the development of a therapeutic foot orthosis, Multi AFO, to hold a foot in a fixed position and prevent heel contract, eliminating decubitus pressure and chafing as well as supporting the foot.

Analysis of current AFO/Contracture products and, indeed, U.S. Pat. No. 5,372,576, indicates the therapeutic importance of the device liner as a means of providing stability and patient comfort. However, the liner can become a hostile healing environment. Current products contain liners made of soft, lofty materials such as fleece, pile or foam. The combination of warmth and moisture creates an ideal breeding ground for certain bacteria, yeasts, and fungi which cause odor. Additionally, these materials can become wet and soiled with various body fluids and thus uncomfortable to the user. The liner must be removed from the device and laundered. As the liner could be highly contaminated, there is risk of cross-contamination if the liner is not properly handled or labeled. Also, the patient must have two liners or be without the benefit of the device for the period of time while the liner is being cleaned.

DESCRIPTION OF THE PRIOR ART

Applicants are aware of the following U.S. Patents concerning splint liners.

| Patent No. | Issued | Inventor | Title |
| --- | --- | --- | --- |
| 5,372,576 | Dec. 13, 1994 | Rickey L. Hicks | Therapeutic Foot Orthosis |
| 6,067,987 | May 30, 2000 | Samuel Scheinberg | Protecting Skin and Other Tissues From Friction |
| 6,056,712 | May 2, 2000 | Tracy E. Grim | Multi-Functional Orthosis for the Foot, Heel, Ankle and Lower Leg |
| 5,853,380 | Dec. 29, 1998 | John J. Miller | Soft Ankle-Foot Orthosis |
| 5,197,942 | Mar. 30, 1993 | Harold Brady | Customized Foot Orthosis |
| 5,151,081 | Sept. 29, 1992 | Paul J. Williams | Foot Splint |
| 5,961,477 | Oct. 5, 1999 | Craig H. Turtzo | Ankle/Foot Orthosis |

| Patent Application Publication No. | Publication Date | Inventor | Title |
| --- | --- | --- | --- |
| 2002/0138029 | Sept. 26, 2002 | Neil R. Bacheldor | Brace Cushion |
| 2001/0031936 | Oct. 18, 2001 | James Pior, et al. | Foot Orthosis |

U.S. Pat. No. 5,372,576 of Rickey L. Hicks is a therapeutic device for attachment to the foot and leg of a user for alleviating and correcting foot deformities, and for maintaining the foot in a fixed, stable, yet comfortable position following surgery or other medical procedure performed on the foot. The device comprises a leg-engaging portion, a foot supporting portion and a heel portion which interconnects and advantageously is integral with the leg and foot portions. The heel portion has an inner and an outer surface and a curvature such that the inner surface of the heel portion can be positioned in sufficient spaced relation to the heel of a user to prevent contact between the inner surface of the heel portion and the heel of the user, thereby to eliminate any chafing, or abrasive contact, or decubitus or pain-inducing pressure between the heel of the user and the inner surface of the heel portion. The side margins of the heel portion are adapted to receive releasable fastening members for engaging the foot of a user whereby the inner surface of the heel portion will be maintained in a stable, fixed position in spaced relation to the heel of a user. A one-piece liner is secured to the inside of the device which acts to provide both optimum comfort to the user and to aid in maintaining the foot of a user in the stable, fixed position established by the releasable fastenings carried on the side margins of the heel portion.

U.S. Pat. No. 6,067,987 of Samuel Scheinberg discloses a tissue-protective device and a method for protecting tissue against abrasion by attaching a pair of mutually overlying membranous layers (26, 28, 122, 124) to an area of a tissue surface such as a person's skin with only the peripheries of the layers being interconnected with each other, so that the layers can easily slip along each other. An absorbent pad (88, 98) may be placed between one of the layers and the tissue, and may be impregnated with medication to be delivered to the tissue being protected. A quantity of a lubricant can be contained between the layers. The device is thin, to avoid causing pressure when it is used in restricted spaces, as within one's shoe. The device can also be implanted internally as where tendons move along an implanted plate.

U.S. Pat. No. 6,056,612, Tracy E. Grim, describes a multi-function orthosis for immobilizing the lower leg, heel, ankle and foot of a human patient, which also provides adjustable therapeutic pressure on the foot sole, and which allows for ambulation. An upper leg unit lined with a pneumatic bladder is adapted to receive the lower leg of the patient and is hingedly attached to a lower, foot base unit which is adapted to receive the foot of the patient. Retractable kickstands attached to the foot base unit extend to prevent outward or inward rolling of the patient's foot, leg and hip, and to also provide protection from the bedding. An extendable foot slide adjusts to support the foot of the patient and to retract when not in use, and an adjustable and retractable toe flap is attached to the foot slide to protect the toes when the patient is immobilized or ambulatory. A low-profile ambulation sled attachable to the bottom of the foot base unit provides a relatively wide platform to allow safe ambulation of the patient without the removal of the orthosis or the aid of other devices.

U.S. Pat. No. 5,853,380 of John J. Miller discloses a soft ankle/foot orthosis for protecting the ankle and foot of a person. In a preferred embodiment, the soft ankle/foot orthosis comprises an outer layer of soft compressible plastic material and an inner layer of soft compressible plastic material. The inner layer of soft compressible plastic material is bonded to the inside of the outer layer of soft compressible plastic material, the inner layer and the outer layer together defining a split shell. The shell is sized and has a molded shape corresponding generally to the lower leg and foot of the person on whom it is to be worn, the lower leg portion and the foot portion of the shell being oriented generally perpendicular to one another to properly position the ankle so as to prevent fractures to the foot and/or ankle. To protect an ulcerative heel and/or ulcerative toes from contact with potentially irritating items, the shell is enlarged in the back and bottom of the heel region and is sized to extend beyond the toes of the person. One or more reinforcing stays are fixedly sandwiched between the inner layer and the outer layer to assist in holding the shell in its molded shape. A plurality of releasable fasteners are used to hold the shell in place on the wearer.

U.S. Pat. No. 5,197,942 of Harold Brady describes a customized foot orthosis designed to be worn by a patient having at least one ulcerated site on his or her foot. The foot orthosis comprises a brace having at least a back portion and a sole portion, an aperture extending through the sole portion, and means for fastening the orthosis securely to the patient's foot and lower leg. The aperture is positioned to correspond with the location of the ulcerated site on the patient's foot, thus relieving pressure from the ulcerated site when the patient is weight-bearing and thereby permitting the patient to be mobile while simultaneously assisting in the aeration and healing of the ulcerated site.

U.S. Pat. No. 5,151,081 of Paul J. Williams shows a foot splint which utilizes an L-shaped plastic splint element having an upstanding leg portion, a heel portion, and a foot portion extending forwardly from the heel portion. A suitable padding material is located on the inside surface of the plastic splint element. A first strap having a figure eight configuration extends from the upper outside portion of the plastic splint element forwardly and downwardly around the bottom of the foot portion, with segments of the strap overlapping each other in spaced relation above the foot portion. The strap is link adjustable for tightening about the foot of the patient. A stabilizer bar is pivotally secured by its upper end to the upper outside surface of the leg portion and is adapted to be pivotally moved in a transverse direction with respect to the leg portion. A pivotal fastener connects the stabilizer bar to the plastic element and is preloading frictionally so that the stabilizer bar under normal conditions will stay at any angle with respect to the plastic splint element to which it is manually moved.

Craig H. Turtzo, in U.S. Pat. No. 5,961,477, discloses a foot and ankle orthosis is adapted for use by a patient in both resting and walking modes. The orthosis includes a generally L-shaped support member which has a leg portion positioned behind the patient's lower leg, a heel portion positioned behind the patient's heel and Achilles' tendon area, and a foot portion positioned substantially entirely against the sole of the patient's foot, when in normal operative use position. The foot portion has an upper surface and a lower surface and the heel portion connects the leg portion and the foot portion. A walking sole plate is releasably connectable to the generally L-shaped support member, to thereby permit optional use by the patient of the walking sole plate in combination with the generally L-shaped support member for facilitating ambulation by the patient. A manually operable locking mechanism is attached to the lower surface of the foot portion of the generally L-shaped support member, to thereby permit rapid, selectively; releasable connection of the walking sole plate to the generally L-shaped support member.

U.S. Pat. No. 5,143,058, George H. Luber, describes a foot and leg splint has two main elements: a hard plastic shell portion and a flexible boot-like garment assembly which cushions the patient's foot and secures the foot to the shell. The shell has a back section shaped to provide comfortable support for the calf and lower leg of the patient. A first portion of the heel section extends straight downward from the back section with a flat back surface to prevent unwanted rocking or rotation of the patient's foot when the patient is in a prone position. A second portion of the heel section extends horizontally, perpendicular to the first section of the heel to form a squared-off heel and provide a flat surface for supporting the heel when the patient is standing or walking. A plantar section extends forward from the second heel portion and curves upward to support the arch of the patient's foot. A toe protector may be provided to extend forward beyond the plantar section. The boot-like garment assembly is provided with pockets to receive each end of the shell and a strap to extend around behind the heel portion of the shell. The boot-like garment has a fleece-like, soft inner-liner which covers much of the patient's foot and calf, and a canvas outer jacket to envelop the inner-liner and protect the patient's foot. Additional straps may be provided to encircle the patient's ankle and upper calf to secure the patient's foot and leg to the shell.

In U.S. Patent Application 2002/0138029 A1, Neil R. Bacheldor discusses a padding or cushioning device adapted to be worn with a leg brace includes a cloth body fabricated from soft, supple material. The cloth body is provided with elastic straps so that it may easily be secured to and removed from the leg brace. The cloth body is disposed between the leg and the brace and functions to insulate the skin of the leg from direct contact with the brace, thereby preventing rubbing and/or chafing.

In U.S. Patent Application 2001/0031936 A1, James Pior describes an orthosis including a splint, a sole member detachably connectable to a surface of the splint, a fastener extending from the surface of the splint, an aperture extending through the sole member for receiving the fastener, a projection extending from the surface of the splint and spaced apart from the fastener, and a receptacle defined on the sole member for receiving the projection in a snap-fit relationship when the sole member is installed on the splint.

SUMMARY OF THE INVENTION

The patent invention is an AFO/contracture foot splint device having a disposable liner. The AFO/contracture foot splint device is used for alleviating and correcting foot deformities, treating foot drop, preventing decubitus ulceration of the calcaneus (heel bone), by maintaining the foot in a stable, yet comfortable, position following surgery or other medical procedure performed on the foot. The device is comprised of a leg-engaging portion, a foot supporting portion, a toe extension portion, a heel portion, and a disposable liner. The device supports and is advantageously integral with the leg and foot portions. The heel portion is positioned to prevent contact between the upper surface of the heel portion of the device and the heel of the wearer, thereby eliminating chafing, abrasive contact, decubitus ulceration, or pain-inducing pressure. The liner is secured to and fitted onto the inner surface of the multi AFO/contracture splint shell, wherein the shell is preferably a unitary curvilinear element encompassing all of the portions. The shell is preferably plastic. The liner is disposable, preferably one piece, with an opening in the heel area. The patient's foot is placed into the AFO and the disposable liner is secured around the leg and foot with hook and loop straps. Additional adjustable straps/flaps can overlap the disposable liner.

The disposable liner is a multi-ply laminate having a breathable, lightweight, non-woven layer, an inner core layer comprised of an absorbent material that provides comfortable padding, and a moisture proof layer. Each of these layers can be comprised of a variety of materials that give acceptable breathability and absorbency characteristics. The moisture-proof layer, being substantially impervious to liquids, is comprised of a material that has a high moisture vapor transmission rate, such that to a certain extent the moisture proof layer can be characterized as breathable. The liner is preferably one piece that is easily attached to the AFO. The liner may be sewn or otherwise constructed using RF (radio frequency—or microwave) sealing. The preferred method of manufacture is RF sealing of edges, as well as attaching hooks, loops and creating heel. The liner has a toe end, foot region, a leg end, a leg region, and a heel region. The toe end is fitted with a toe pocket that slips over the toe extension portion of the splint's shell. The leg end of the liner has a leg pocket that fits onto the leg engaging portion of the splint's shell. The foot region has winged extensions terminated with fastening elements, such as hook and loop fasteners. The winged extensions can be folded over the foot and fastened, thereby securing the foot region of the disposable liner to the foot. The leg end of the liner has tabular extensions terminated with re-closable fastening elements, such as hook and loop fasteners. The tabular extensions can be folded around the calf of the leg and fastened, thereby securing the leg region of the disposable liner to the leg. The heel region of the liner has an opening, which enables a portion of the wearer's heel to project through the heel region. The heel of the wearer is exposed and suspended over the heel "well" of the plastic shell. The liner on either side of the heel opening is gathered and stitched or welded to draw the foot of the liner upward to the correct angle and eliminate bulkiness and pressure points.

The liner material preferably contains an anti-microbial additive, such as triclosan. Triclosan is a diphenyl ether (bis-phenyl) derivative, known as either 2,4,4'-trichloro-2'-hydroxydiphenyl ether or 5-chloro-2-(2,4-dichlorophenoxy) phenol. It is believed that its antimicrobial properties are derived by blocking an enzyme, known as enoyl-acyl carrier-protein reductase (a.k.a. ENR). ENR prevents bacteria from manufacturing the fatty acids microbial agents require for building cell membranes and other vital functions. Humans don't have this enzyme, so triclosan is believed to be harmless to them. One molecule of triclosan permanently disables an ENR molecule and, therefore, is a powerful antibiotic, even at very low concentrations.

OBJECTS OF THE INVENTION

The principal object of the present invention is to provide a disposable liner for splints and other AFO devices.

A second object of the invention is to minimize risks associated with cleaned reusable liners, where cleaned reusable liners have a potential for residual microbial infection.

Another object of this invention is to reduce risks associated with wearing soiled or wet liners that can act as media for supporting microbial growth.

Another object of the invention is to provide a clean, comfortable liner for the user by providing a single use liner that can be discarded and easily replaced as necessary.

Another object of the invention is to eliminate the discomfort from wet liners through the selection of a material that contains a permeable, protective layer next to the skin, an absorbent anti-microbial core layer that pulls moisture away form the skin, and a moisture proof backing to contain fluids.

Another object of the invention is to disclose the physical features of a disposable liner suitable for splints and other AFO devices.

Another object of the invention is to disclose the chemical composition of a disposable liner suitable for splints and other AFO devices.

BRIEF DESCRIPTION OF THE DRAWINGS

The foregoing and other objects will become more readily apparent by referring to the following detailed description and the appended drawings in which:

FIG. 2 is a planar view of the invented disposable liner, wherein inclusive in the FIG. 2 is a partially cutaway sectional view illustrating the layers of the liner.

DETAILED DESCRIPTION

Figure 1:
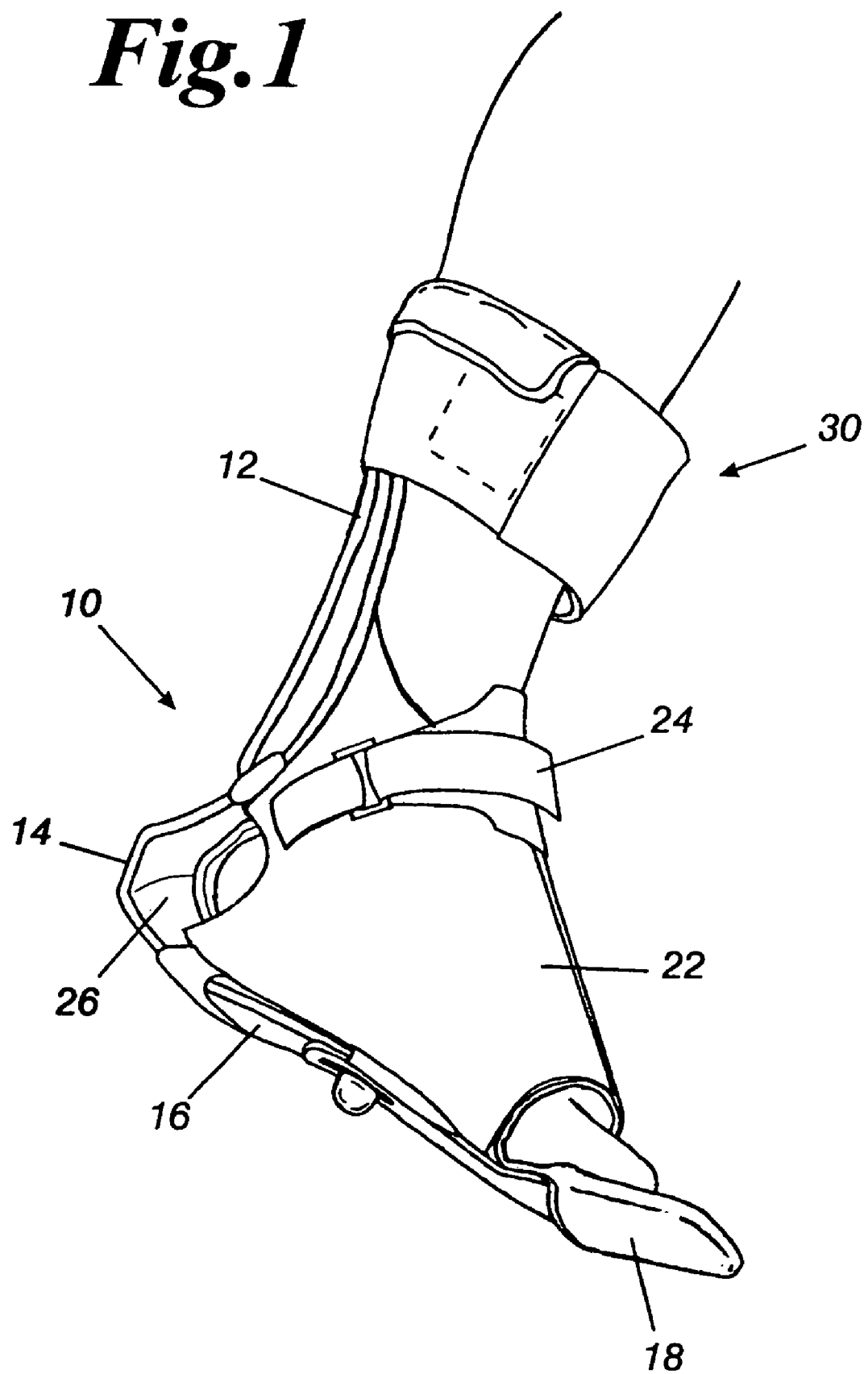
FIG. 1 is an isometric view of a multi AFO/Contracture Splint with a disposable liner.

Referring now to the drawings, and particularly to FIG. 1, the invented AFO/contracture foot splint device 10 has a disposable liner 30. The AFO/contracture foot splint device is for alleviating and correcting foot deformities, treating foot drop, preventing decubitus ulceration of the calcaneus (heel bone), by maintaining the foot in a stable, yet comfortable position, following surgery or another medical procedure performed on the foot. The device has a leg-engaging portion 12, a foot supporting portion 16, a toe extension portion 18, a heel portion 14, and a disposable liner 30. The heel portion is distended forming a well 26 to prevent contact between the upper surface of the heel portion 14 of the splint device 10, thereby eliminating chafing, or abrasive contact, which can cause decubitus ulceration or pain-inducing pressure. The liner 30 is secured to and fitted onto the inner surface of the multi AFO/contracture splint shell, wherein the shell is preferably a unitary curvilinear element cumulatively inclusive of all of the portions (e.g. the leg engaging portion 12, the foot supporting portion 16, the toe extension portion 18, the heel portion 14). The shell is a resilient engineering plastic. The splint 10 has a supporting flexible flap 22 and an adjustable strap 24. Referring to FIG. 2, the disposable liner 30 is a multi-ply laminate of a breathable, lightweight, non-woven layer 76, an inner core layer 74 comprised of an absorbent material that provides comfortable padding, and a moisture proof layer 72. The moisture proof layer 72 is impervious to liquids, is comprised of a plastic material that has a high moisture vapor transmission rate. The liner 30 is a die cut single piece, having RF sealed seams 70 that define the perimeter and the opening 58 in the heel. The disposable liner 30 has a toe end 32, foot region 34, a leg end 38, a leg region 36, and a heel region 56. The toe end 32 is fitted with a toe pocket 40 that slips over the toe extension portion 18 of the splint's shell. The leg end 38 of the liner has a leg pocket 42 that fits onto the leg engaging portion 12 of the splint's shell. The foot region 34 has a pair of winged extensions, 46 and 44, terminated with a set of fastening elements 52 and 54, which are hook 52 and loop 54 fasteners, respectively. The winged extensions, 46 and 44, are folded over the foot and fastened, thereby securing the foot region of the disposable liner to the foot. The leg region 38 of the liner has a set of tabular extensions, 50 and 48, terminated with re-closable fastening elements, 60 and 62, which are hook 60 and loop 62 fasteners, respectively. The tabular extensions, 60 and 62, are wrapped around the calf of the leg and fastened, thereby securing the leg region 36 of the disposable liner to the leg. The heel region 56 of the liner has an opening 58, which enables a portion of the wearer's heel to project through the heel region. The heel of the wearer is exposed and suspended over the heel well 26 of the plastic shell. The right and left sides the disposable liner are longitudinally identical, except for the fastening elements 60, 62, 52 and 54, so that a the disposable liner can be used for either the right or the left AFO.

The disposable liner 30 is sufficiently soft and flexible to conform comfortably to body surfaces and provide for a substantially close fit to prevent leakage. The fluid permeable layer 76 is made to be in contact with a body surface. The cover is made of a material that allows the unimpeded transfer of fluid from the body into the core of the liner. The fluid permeable layer should not absorb fluid per se and, thus, should remain dry. The moisture-proof layer is a liquid impervious back sheet disposed on the outer surface of the liner, and is fabricated to prevent the leakage of fluids. The moisture-proof layer 72 is breathable, and preferably has a high MVTR. Disposed between the fluid permeable layer 76 and the moisture-proof layer 72 is the absorbent layer 74. The function of the absorbent layer is to absorb and retain body fluids entering the disposable liner through the fluid permeable layer. Because the origin of body fluids tends to be localized, it is necessary to provide a means for distributing fluid throughout the dimensions of the absorbent layer to make full use of all the available absorbent material. This is accomplished either by providing a distribution member disposed between the fluid permeable layer and absorbent layer and/or altering the composition of the absorbent layer, for instance by adding a strata containing superabsorbent. Fluid can be distributed to different portions of the absorbent layer by means of a transfer or acquisition layer (not shown) disposed between the fluid permeable and absorbent layer. The purpose of the acquisition layer is to provide for rapid transfer and distribution of fluid to the absorbent layer while minimizing spread of the fluid in this layer.

The absorbent layer is, preferably, formulated of a cellulosic wood fiber matrix or pulp, which pulp is capable of absorbing large quantities of fluid. Fluid retention characteristics of the absorbent layer are enhanced by disposing superabsorbent materials amongst the fiber matrix. Superabsorbent materials are substantially water-insoluble, absorbent polymeric compositions that are capable of absorbing large amounts of fluid in relation to their weight. Additionally, the absorbent layer can contain complex forming agents that are, for example, polymeric olefins and polyacids. These complex forming agents are cationic and anionic binders that serve to hold the superabsorbent material within the material.

In one embodiment, a material for use in the absorbent layer has three strata: a bottom layer of pulp (without superabsorbent) with a basis weight of about 50 $g/m^2$; a middle layer with a basis weight of about 300 $g/m^2$ and which contains from about 20 $g/m^2$ to about 60 $g/m^2$ superabsorbent and from about 240 $g/m^2$ to about 280 $g/m^2$ pulp; and a top layer of pulp (without superabsorbent) with a basis weight of about 50 $g/m^2$. Relative to the total basis weight of the material, the level of superabsorbent ranges from about 5 to about 15 weight percent ($g/m^2$ of superabsorbent per $g/m^2$ material). Preferably, the level of superabsorbent is from about 7.5 weight percent to about 12.5 weight percent of the material. Most preferably, the material contains about 10 weight percent of superabsorbent. Thus, the middle layer of the material preferably contains from about 30 $g/m^2$ to about 50 $g/m^2$ superabsorbent and from about 250 $g/m^2$ to about 270 $g/m^2$ pulp and, more preferably about 40 $g/m^2$ superabsorbent and about 260 $g/m^2$ pulp. The middle layer containing pulp and superabsorbent can be laid down as a homogeneous blend or as a heterogeneous blend wherein the level of superabsorbent varies with proximity to the bottom layer.

SUMMARY OF THE ACHIEVEMENTS OF THE OBJECTS OF THE INVENTION

From the foregoing, it is readily apparent that we have invented a disposable liner for splints and other AFO devices, which minimize risks associated with cleaned reusable liners, where cleaned reusable liners have a potential for residual microbial infection. The invention reduces risks associated with wearing soiled or wet liners which can be media for supporting microbial growth. Disposable liners provide a clean, comfortable liner for the user by providing a single use liner that can be discarded and easily replaced as necessary, by minimizing discomfort from wet liners through the selection of a material that contains an absorbent anti-microbial core layer that pulls moisture away form the skin, and a moisture proof backing to contain fluids.

It is to be understood that the foregoing description and specific embodiments are merely illustrative of the best mode of the invention and the principles thereof, and that various modifications and additions may be made to the apparatus by those skilled in the art, without departing from the spirit and scope of this invention, which is therefore understood to be limited only by the scope of the appended claims.

What is claimed is:

1. An AFO/contracture foot splint device for alleviating and correcting foot deformities, treating foot drop, preventing decubitus ulceration of the calcaneus (heel bone), by maintaining the foot in a fixed, stable, yet comfortable position following surgery or other medical procedure performed on the foot, said device comprising
   a) a leg engaging portion;
   b) a foot supporting portion;
   c) a heel portion having a heel well;
   d) a toe extension portion
   e) a disposable liner;
   wherein the heel portion prevents contact between an upper surface of the heel portion of the device and the heel of the wearer thereby eliminating chafing, or abrasive contact, or decubitus ulceration, or pain-inducing pressure;
   wherein said disposable liner is a single piece that extends from the toe extension portion to the leg engaging portion of the AFO/contracture foot splint device, said single piece having a leg pocket (42) and a toe pocket (40), where said leg pocket (42) fits onto the leg engaging portion and said toe pocket (40) fits onto said toe extension portion, thereby securing the disposable liner to the splint device;
   wherein said disposable liner has re-closable fastening elements to secure said disposable liner to the leg and the foot; and
   wherein the disposable liner is comprised of a fluid permeable layer, an absorbent layer and moisture proof layer.

2. The AFO/contracture foot splint device as claimed in claim 1, wherein said disposable liner further comprises an antimicrobial additive.

3. The AFO/contracture foot splint device as claimed in claim 2, wherein said antimicrobial additive is triclosan.

4. The AFO/contracture foot splint device as claimed in claim 1, wherein the leg engaging portion, the heel portion, the foot supporting portion, and the toe extension portion comprise a shell.

5. The AFO/contracture foot splint device as claimed in claim 4, wherein said loop straps are affixed to the moisture proof layer.

6. The AFO/contracture foot splint device as claimed in claim 5, wherein said disposable liner has a heel area that is cut out forming a heel opening, wherein the heel opening is gathered and stitched or welded to draw the foot of the liner upward to the correct angle and eliminate bulkiness and pressure points.

7. The AFO/contracture foot splint device as claimed in claim 5, wherein said device is further provided with additional adjustable straps attached to flaps which overlap the disposable liner.

8. The AFO/contracture foot splint device according to claim 1, wherein said absorbent layer is a multi-strata layer of a relatively high level of a superabsorbent in a stratum, and a high level of a cellulosic wood fiber matrix or pulp in an adjacent stratum.

9. The AFO/contracture foot splint device as claimed in claim 8, wherein said disposable liner incorporates an antimicrobial additive therein.

10. The AFO/contracture foot splint device as claimed in claim 9, wherein said antimicrobial additive is triclosan.

11. The AFO/contracture foot splint device as claimed in claim 1, wherein said re-closable fastening elements are has hook and loop straps on the moisture proof layer to secure said disposable liner to the leg and the foot.

12. A liner for an AFO/contracture foot splint device, wherein said liner is a disposable liner that is sufficiently soft and flexible so as to comfortably conform to body surfaces and provide for substantially a close fit to prevent leakage, said liner comprising:
   a) a fluid permeable layer;
   b) an absorbent layer, the function of the absorbent layer is to absorb and retain body fluids entering the disposable liner through the fluid permeable layer;
   c) a moisture proof layer which is a liquid impervious back sheet disposed on the outer surface of the liner, and is designed to prevent the leakage of fluids;
   wherein said disposable liner is a single piece that, when fitted to the AFO/contracture foot splint device, extends from a toe extension portion to a leg engaging portion of the AFO/contracture foot splint device, said single piece having a leg pocket (42) and a toe pocket (40), where said leg pocket (42) fits onto the leg engaging portion and said toe pocket (40) fits onto said toe extension portion, thereby securing the liner to the splint device; and
   wherein the moisture proof layer is breathable and has a high MVTR.

13. The liner for an AFO/contracture foot splint device, as claimed in claim 12, wherein said liner is further comprised of:
   a) a toe end;
   b) a foot region;
   c) a leg end;
   d) a leg region;
   e) a heel region;
   wherein the foot region has winged extensions terminated with fastening elements, said winged extensions being foldable over the foot and fastened, thereby securing the foot region;
   wherein the leg end of the liner has tabular extensions terminated with re-closable fastening elements, said tabular extensions being foldable around the calf of the leg and fastened, thereby securing the leg region of the disposable liner to the leg;
   wherein said heel region of the liner has an opening, which enables a portion of a wearer's heel to project through the heel region into a heel "well" of the splint device; and
   wherein the liner on either side of the heel opening is gathered and stitched or welded to draw the foot of the liner upward to the correct angle and eliminate bulkiness and pressure points.

14. The liner for an AFO/contracture foot splint device, as claimed in claim 13, wherein the absorbent layer is comprised of a cellulosic wood fiber matrix or pulp, which pulp is capable of absorbing large quantities of fluid.

15. The liner for an AFO/contracture foot splint device according to claim 14, wherein the absorbent layer is further comprised of a superabsorbent amongst the fiber matrix.

16. The liner for an AFO/contracture foot splint device according to claim 15, wherein the absorbent layer is further comprised of complex forming agents, which are cationic and anionic binders for the superabsorbents.

17. The liner for an AFO/contracture foot splint device according to claim 13, wherein the absorbent layer is further comprised of an antimicrobial additive.

18. The liner for an AFO/contracture foot splint device according to claim 17 wherein said antimicrobial additive is triclosan.

* * * * *